United States Patent [19]

Owen et al.

[11] 4,071,573
[45] Jan. 31, 1978

[54] PROLONGING ZEOLITE CATALYST LIFE IN METHANOL CONVERSION TO GASOLINE BY DISPOSING OF EXOTHERMIC REACTION HEAT

[75] Inventors: Hartley Owen, Belle Mead; Paul B. Venuto, Cherry Hill, both of N.J.

[73] Assignee: Mobil Oil Corporation, New York, N.Y.

[21] Appl. No.: 733,981

[22] Filed: Oct. 20, 1976

Related U.S. Application Data

[63] Continuation of Ser. No. 506,157, Sept. 23, 1974, abandoned, which is a continuation-in-part of Ser. No. 470,084, May 15, 1974, abandoned.

[51] Int. Cl.² ............................................. C07C 15/02
[52] U.S. Cl. .................................. 260/668 R; 208/143; 260/682
[58] Field of Search ..................... 260/668; 208/143

[56] References Cited

U.S. PATENT DOCUMENTS

| | | | |
|---|---|---|---|
| 2,382,382 | 8/1945 | Carlsmith et al. | 252/417 |
| 2,394,710 | 2/1946 | McAfee | 208/118 |
| 2,418,003 | 3/1947 | Angell | 208/118 |
| 3,471,582 | 10/1969 | Lupfer | 208/143 |
| 3,894,107 | 7/1975 | Butler | 260/668 R |

Primary Examiner—Veronica O'Keefe
Attorney, Agent, or Firm—Charles A. Huggett; Carl D. Farnsworth

[57] ABSTRACT

A method for effecting chemical reactions of aliphatic hetero compounds comprising alcohols, halides, mercaptans, sulfides, amines, ethers and carbonyl compounds with a fluidized crystalline zeolite catalyst and regeneration of a portion of the catalyst used in the fluid catalyst operation is described. Catalyst recycle to each of the catalyst contact zones is particularly employed.

4 Claims, 3 Drawing Figures

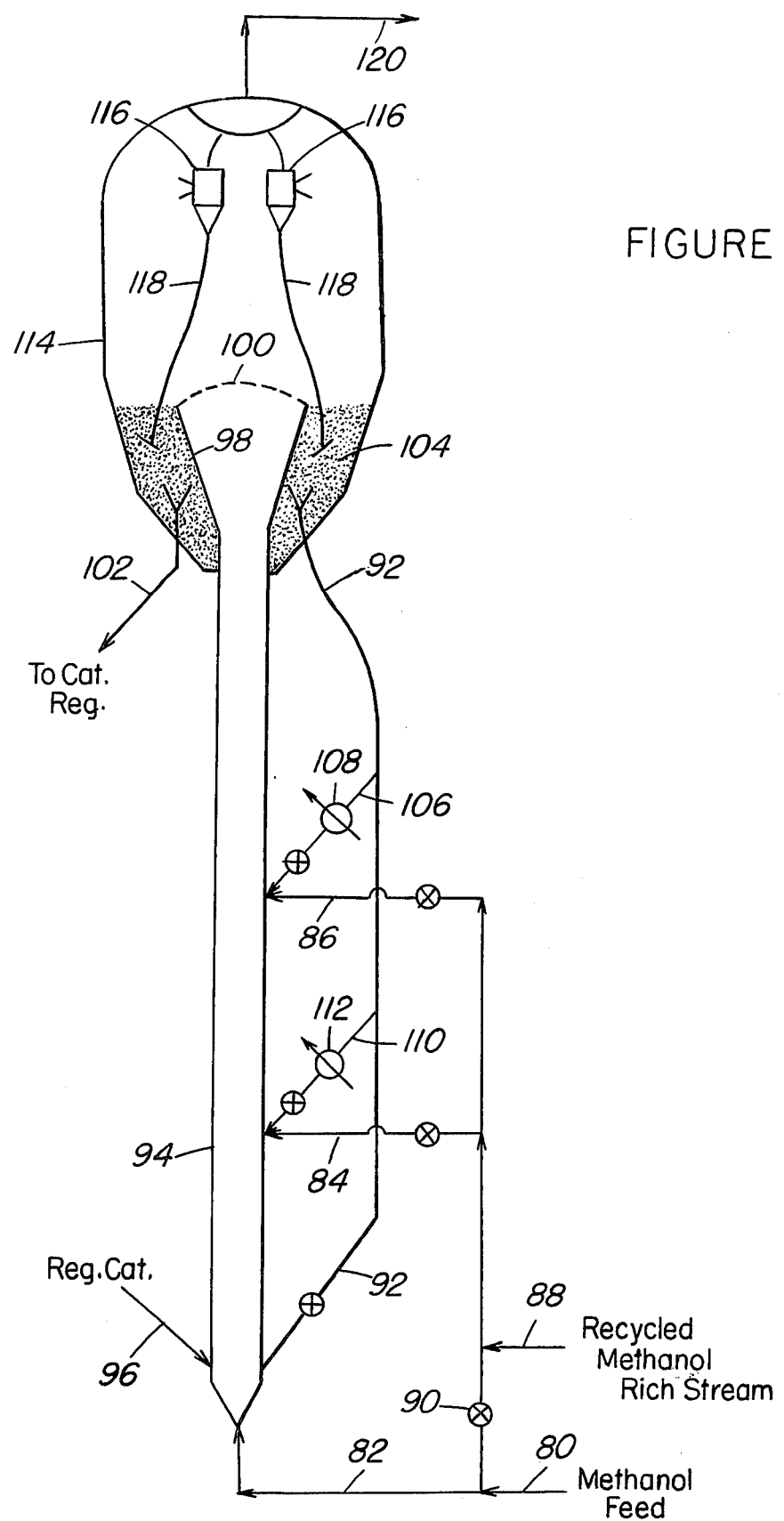
FIGURE II

FIGURE III
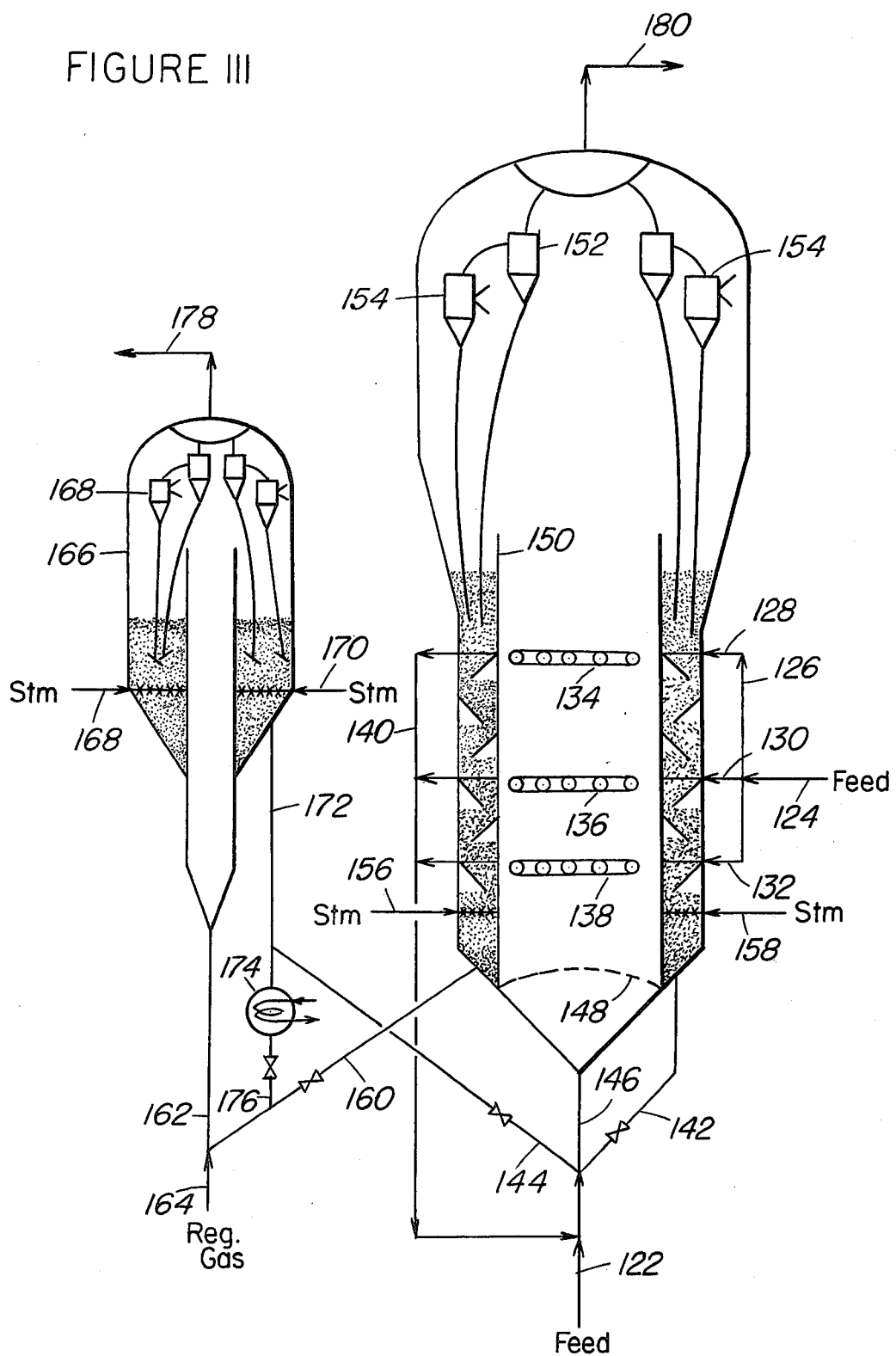

PROLONGING ZEOLITE CATALYST LIFE IN METHANOL CONVERSION TO GASOLINE BY DISPOSING OF EXOTHERMIC REACTION HEAT

This application is a continuation of application Ser. No. 506,157 filed Sept. 23, 1974, now abandoned which in turn is a continuation-in-part of application Ser. No. 470,084 filed May 15, 1974 now abandoned.

BACKGROUND OF THE INVENTION

The application of fluidized-catalyst techniques developed particularly in the petroleum industry for effecting chemical reaction embodying the distribution of heat and/or the disposal of undesired heat has long been accepted as a major processing tool of the industry. For example, the catalytic cracking of oil vapors to produce lower boiling desired products and regeneration of the catalyst used in such an operation has been particularly useful of fluidized catalyst techniques. It has also been proposed to use the fluidized catalyst technique in the highly exothermic reactions of Fischer-Tropsch synthesis and the known Oxo process primarily for the disposal of generated heat. In many of the fluidized catalyst operations developed, disposal of the reaction heat has been accomplished by many differet techniques including transfer of catalyst through cooling sections and/or including indirect cooling means with a fluid bed of catalyst to adsorb reaction heat transferred by the finely divided fluidized catalyst particles. Not only is the fluidized catalyst technique used for temperature control by addition and/or removal but it has also been found useful for extending the active life of the catalyst used in the process.

The present invention is concerned with an arrangement and method of operation for disposing of generated exothermic reaction heat within limits which will particularly protect and prolong the useful life of the catalyst employed in the operation.

SUMMARY OF THE INVENTION

This invention relates to the method and means for effecting chemical reactions in the presence of a select class of particulate crystalline zeolites. More particularly, the present invention is concerned with effecting exothermic chemical reactions in the presence of crystalline zeolites of selected crystal arrangement particularly promoting the formulation of hydrocarbon product materials higher boiling than the reactant charge material. In a more particular aspect, the present invention is concerned with effecting the conversion of methanol and derivatives thereof in a fluid bed of particulate material providing a crystalline zeolite with a pore dimension greater than about 5 Angstroms and pore windows of a size provided by 10 membered rings of oxygen atoms. In a more particular aspect, the present invention is concerned with the method and means for effecting the conversion of compounds of carbon and hydrogen with and without combined oxygen in a fluid bed of catalyst particles to higher boiling products in the gasoline boiling range.

A novel class of crystalline zeolites has been found which induces profound transformations of simple carbon-hydrogen compounds to more complex hydrocarbon structures and aromatic hydrocarbons in commercially desirable yields. Although these zeolites have a low alumina content, i.e. high silica to alumina ratios, they are very active even when the silica to alumina ratio particularly exceeds about 30. These particular crystalline zeolites retain their crystallinity for long operating periods in spite of the presence of steam at high temperature which heretofore was considered to induce irreversible collapse of the framework of other zeolites, e.g. of the X and A type. Furthermore, carbonaceous deposits, when formed, may be removed by burning at high temperatures to restore activity.

An important characteristic of the crystal structure of this novel class of zeolites is that it provides constrained access to, and egress from, the intracrystalline free space by virtue of having a pore dimension greater than about 5 Angstroms and pore windows of a size provided by 10-membered rings of oxygen atoms. It is to be understood, of course, that these rings are those formed by the regular disposition of the oxygen of the tetrahedra making up the anionic framework of the crystalline aluminosilicate, the oxygen atoms themselves being bonded to the silicon or aluminum atoms at the centers of the tetrahedra. Briefly, the preferred novel type or class of crystalline zeolite catalyst useful in this invention possess, in combination: a silica to alumina ratio of at least about 12; and a structure providing constrained access to the crystalline free space.

The silica to alumina ratio referred to may be determined by known analysis techniques. This silica-alumina ratio is meant to represent, as closely as possible, the ratio in the rigid anionic framework of the zeolite crystal and to exclude aluminum in the binder or in cationic form within the channels. Although catalysts with a silica to alumina ratio of at least 12 are useful, it is preferred to use catalysts having higher ratios of at least about 30. Such catalysts, after activation, acquire an intracrystalline sorption capacity for normal hexane which is greater than that for water, i.e. they exhibit "hydrophobic" properties.

The type of zeolites useful in this invention freely sorb normal hexane and have a pore dimension greater than about 5 Angstroms. In addition, the structure must provide constrained access to larger molecules. It is sometimes possible to judge from a known crystal structure whether such constrained access exists. For example, if the only pore windows in a crystal are formed by eight membered rings of oxygen atoms, then access to molecules of larger cross-section than normal hexane is excluded and the zeolite is not of the desired type. Windows of ten-membered rings are preferred, although excessive puckering or pore blockage may render these catalysts ineffective. Twelve-membered oxygen rings do not generally appear to offer sufficient constraint to produce the advantageous conversions, although structures can be conceived, due to pore blockage or other cause, that may be operative.

Rather than attempt to judge from crystal structure whether or not a catalyst possesses the necessary constrained access, a simple determination of the "constraint index" may be made by passing continuously a mixture of equal weight of normal hexane and 3-methylpentane over a small sample, approximately 1 gram or less, of catalyst at atmospheric pressure according to the following procedure. A sample of the catalyst, in the form of pellets or extrudate, is crushed to a particle size about that of coarse sand and mounted in a glass tube. Prior to testing, the catalyst is treated with a stream of air at 1000° F. for at least 15 minutes. The catalyst is then flushed with helimum and the temperature adjusted between 550° and 950° F. to give an overall conversion between 10 and 60%. The mixture of hydrocarbons is passed at 1 liquid hourly space velocity (i.e. 1 volume of hydrocarbon per volume of catalyst per hour) over the catalyst with a helium dilution to give a helium to total hydrocarbon mole ratio of 4:1. After 20 minutes on stream, a sample of the effluent is taken and analyzed, most conveniently by gas chromatography, to determine the fraction remaining unchanged for each of the two hydrocarbons.

The "constraint index" is calculated as follows:

$$\text{Constraint Index} = \frac{\log_{10} \text{ (fraction of n-hexane remaining)}}{\log_{10} \text{ (fraction of 3-methylpentane remaining)}}$$

The constraint index approximates the ratio of the cracking rate constants for the two hydrocarbons. Catalysts suitable for the present invention are those having a constraint index from 1.0 to 12.0, preferably 2.0 to 7.0.

The class of crystalline zeolites defined herein is exemplified by ZSM-5, ZSM-11, ZSM-12, ZSM-21, TEA mordenite and other similar materials. Recently issued U.S. Pat. No. 3,702,886 describing and claiming ZSM-5 is incorporated herein by reference.

ZSM-11 is more particularly described in U.S. Pat. No. 3,709,979, the entire contents of which are incorporated herein by reference.

ZSM-12 is more particularly described in West German Offenlagunschrift No. 2,213,109, the entire contents of which are incorporated herein by reference.

ZSM-21 is more particularly described in U.S. application Ser. No. 358,192, filed May 7, 1973, the entire contents of which are incorporated herein by reference.

TEA mordenite is more particularly described in U.S. application Ser. No. 130,442 filed Apr. 11, 1971, the entire contents of which are incorporated herein by reference.

The specific crystalline zeolites described, when prepared in the presence of organic cations, are catalytically inactive, possibly because the intracrystalline free space is occupied by organic cations from the forming solution. They may be activated by heating in an inert atmosphere at 1000° F. for 1 hour, for example, followed by base exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base exchange with ammonium salts followed by calcination in air at about 1000° F. for from about 15 minutes to about 24 hours.

Natural zeolites may sometimes be converted to this type of zeolite catalyst by various activation procedures and other treatments such as base exchange, steaming, alumina extraction, calcination and combinations thereof. Naturally occurring minerals which may be so treated include ferrierite, brewsterite, stillbite, dachiardite, epistilbite, heulandite and clinoptilolite. The preferred crystalline aluminosilicates are ZSM-5, ZSM-11, ZSM-12, ZSM-21 and TEA mordenite, with ZSM-5 particularly preferred.

The catalysts useful in this invention may be in the hydrogen form or they may be base exchanged or impregnated to contain ammonium or a metal cation complement. It is desirable to calcine the catalyst after base exchange. The metal cations that may be present include any of the cations of the metals of Groups I through VIII of the periodic table. However, in the case of Group IA metals, the cation content should in no case be so large as to effectively inactivate the catalyst. For example, a completely sodium exchanged H-ZSM-5 is not catalytically operative.

In a preferred aspect, the catalysts are selected from those having a crystal density, in the dry hydrogen form, of not substantially below about 1.6 grams per cubic centimeter. It has been found that zeolites which satisfy the criteria herein identified are most desired because they tend to maximize the production of gasoline boiling range hydrocarbon products. Therefore, a preferred catalyst is one having a constraint index as defined above and selected from within the range of about 1 to 12, a silica to alumina ratio of at least about 12 and a dried crystal density of not less than about 1.6 grams per cubic centimeter. The dry density for known structures may be calculated from the number of silicon plus aluminum atoms per 1000 cubic Angstroms, as given, e.g. on page 11 of the article on Zeolite Structure by W. M. Meier. This paper, the entire contents of which are incorporated herein by reference, is included in "Proceedings of the Conference on Molecular Sieves, London, April 1967," published by the Society of Chemical Industry, London, 1968. When the crystal structure is unknown, the crystal framework density may be determined by classical pyknometer techniques. For example, it may be determined by immersing the dry hydrogen form of the zeolite in an organic solvent which is not sorbed by the crystal. It is possible that the unusual sustained activity and stability of this class of zeolites is associated with its high crystal anionic framework density of not less than about 1.6 grams per cubic centimeter. This high density of course must be associated with a relatively small amount of free space within the crystal, which might be expected to result in more stable structures. This free space, however, is important as the locus of catalytic activity.

A remarkable and unique attribute of the class of zeolites above identified is the ability to convert paraffinic hydrocarbons to aromatic hydrocarbons in exceptionally attractive yields by contact at temperatures selected from within the range of 800° to about 1500° F. relying upon space velocities within the range of 1 to 15 weight hourly space velocity (WHSV). This class of crystalline zeolite appears to exert little, if any, action upon destroying aromatic rings either present in the feed or formed in the operation. They do however have the ability, with or without added hydrogen to cause paraffin fragments to dimerize and/or cyclize and also to alkylate aromatic rings either charged or formed in the operation. It appears that the operative ranges for alkylation and formation of new aromatic rings overlap but that the optimum ranges are relatively distinct; aromatization occurring at a higher temperature.

In patent application Ser. No. 387,223, filed Aug. 9, 1973, now U.S. Pat. No. 3,894,107, there is described a process for converting various aliphatic hetero compounds comprising alcohols, halides, mercaptans, sulfides and/or amines to their corresponding analogous compounds and aromatics with a ZSM-5 type of crystalline zeolite. The aromatization of alcohols is particularly discussed.

In patent application Ser. No. 387,222, filed Aug. 9, 1973, now U.S. Pat. No. 3,894,106, there is described a process for converting particularly aliphatic ethers to higher molecular weight materials such as gasoline by contact with a ZSM-5 type of crystalline zeolite.

In patent application Ser. No. 387,224, filed Aug. 9, 1973, now U.S. Pat. No. 3,907,915, there is described a process for converting carbonyl type compounds such as acetone to aromatics and higher boiling materials by contact with a ZSM-5 type of crystalline zeolite.

The subject matter and contents of the above identified applications are intended to be incorporated herein by reference thereto.

The present invention is concerned with the method and system for effecting the exothermic conversion of hetero type compounds, ethers and carbonyl compounds referred to in the above identified applications in a manner particularly promoting the formation of aromatic compounds. More particularly, the present invention is concerned with the method and system for dispersing the exothermic heat of chemical reaction generated in the preparation of aromatics and related compounds by contacting a ZSM-5 type crystalline zeolite with one or more reactants selected from the group consisting of alcohols, ethers and carbonyl compounds.

A more clear and complete understanding of the present invention may be had by reference to the attached drawings.

BRIEF DESCRIPTION OF THE DRAWINGS

FIG. I is a diagrammatic sketch in elevation of one arrangement of apparatus and system comprising a dispersed catalyst phase upflowing conversion zone provided with gas bubble dispersing means at spaced apart intervals, a catalyst regeneration system, means for recycling used catalyst to the reactor inlet and a product recovery system.

FIG. II is a diagrammatic sketch in elevation of an upflowing dispersed catalyst phase system for effecting exothermic reactions and provided with means for recycling catalyst separated from products of reaction at spaced apart intervals to the upflowing catalyst with and without admixture with reactant feed.

Figure 1:
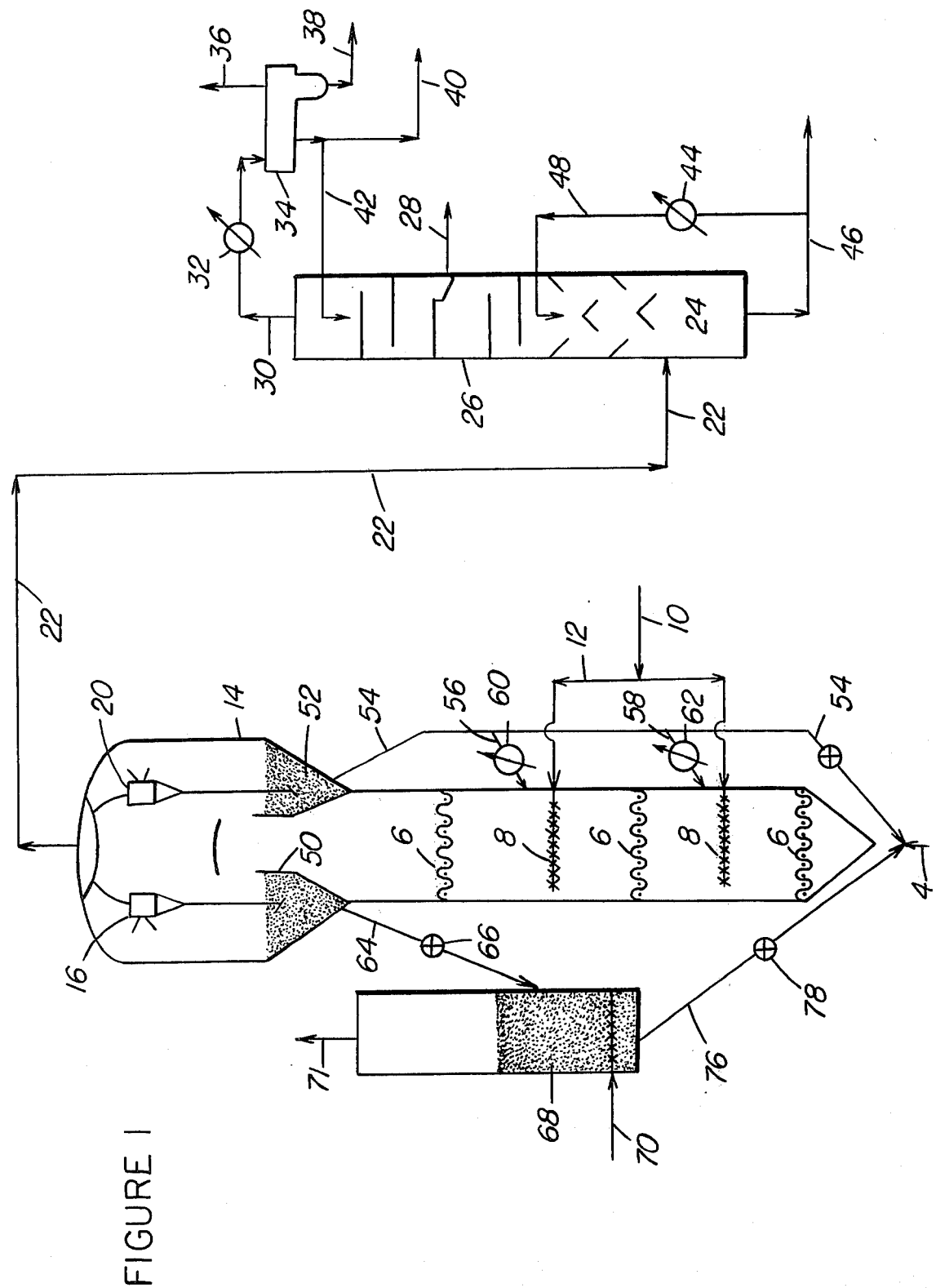

FIG. III is a diagrammatic sketch in elevation of a modification of the system of FIG. I to provide for recycle of regenerated catalyst particles to the regeneration system, cooling of the recycled regenerated catalyst before admixture with spent catalyst passed to the regenerator and means for preheating the feed in gas bubble dispersing tubes at one or more separate spaced apart sections of the reaction zone through which the upflowing dispersed phase of catalyst passes under exothermic reaction conditions.

Referring now to the FIG. I by way of example, there is shown a substantially vertical reactor vessel 2 of relatively large height to diameter ratio through which a mixture or suspension of reactants and fluidizable catalyst particles upwardly pass in a dispersed catalyst phase condition under controlled exothermic reaction conversion conditions. A mixture of catalyst particles comprising recycled and regenerated particles with reactant material is formed and passed through a short riser mixing zone represented by conduit 2 feeding or discharging into the bottom of the enlarged upflowing catalyst suspension reaction vessel. The suspension is initially formed under conditions to provide a mix temperature of about 400° to 900° F. preferably less than 800° F. which is passed through the lower bottom conical portion of the reactor vessel for flow upwardly therethrough as a more dense dispersed phase of upflowing catalyst in reactant material. Recycling of reactant and products of reaction within the upflowing suspension is desirably avoided. Vessel 2 is provided with a plurality of grid means 6 or other suitable open space grid means, wire mesh screens resembling bed springs or horizontal grid forming heat exchange means which means are placed across the vessel at selected spaced apart vertical intervals for the purpose of dispersing any reactant gas or product bubbles formed in the catalyst-reactant suspension passing upwardly through the reaction vessel. In addition, to supplement control of exothermic temperatures generated within the reactor vessel a plurality of quench gas distributor means 8 are placed in the reactor vessel cross-section and vertically spaced apart from one another in a desired arrangement for injecting a quench fluid thus permitting an alternate or additional method for controlling incremental temperature increases not to exceed about 100° in the upflowing suspension. The quench gas distributors are placed adjacent to or intermediate the grid means and thus provide additional gas bubble dispersing means within the vessel. The dispersal of the exothermic reaction heat is accomplished by high catalyst recycle rates in combination with heat exchange and dispersal of quench fluid in the upflowing fluidized catalyst suspension. This dispersal of generated exothermic heat is also influenced by the mixing means and gas bubble dispersing means provided in the upflowing suspended catalyst within the reactor vessel. It is preferred that the grid means, quench gas and/or liquid distributing means be positioned with respect to one another in the vessel height and in an amount which will assure that a delta temperature increase does not exceed about 100° above the reaction temperature desired and is preferably less than 100°.

In the conversion of methanol and related hetero compounds contemplated by this invention the exothermic temperature buildup will be greater than that contributed by the conversion of ethers and carbonyl compounds. On the other hand, when carbon monoxide and/or hydrogen is combined with any one of these reactant feeds there will be a proportional increase in exothermic heat release as a function of these materials reacting with one another and/or the other feeds comprising alcohols, ethers and carbonyl compounds. In any event, it is proposed to maintain a very close temperature control on the sequence of reactions promoted by the ZSM-5 type crystalline zeolite; it being preferred to restrict the conversion of methanol to aromatics to a temperature within the range of 500° to 900° F; the conversion of ethers to aromatics to a temperature within the range of 500° to 900° F.; and the conversion of the carbonyl type feed to a temperature within the range of 500° to 900° F. The operating pressure for these various reactions may be confined within the range of 0 to 200 psig, more usually from 15 to 100 psig and preferably < 50 psig. The reactant space velocity is preferably selected from within the range of 0.1 to 70 v/v/hr. to provide a reactant residence time in contact with the catalyst within the limits of 2 to 300 seconds.

In the arrangement of FIG. I, a reactant feed comprising C.P. grade methanol in a specific example is introduced along with finely divided fluidizable ZSM-5 type crystalline material containing catalyst particles by conduit 4 to the bottom conical portion of reactor vessel 2. Conduit 4 provides a limited reaction time and mixing to occur before discharge into a larger diameter upflowing catalyst suspension reaction zone. The suspension thus formed is caused to pass upwardly through the conical bottom section and through a gas bubble dispersing grid catalyst-reactant distributing means before encountering a relatively more dense upflowing dispersed fluid phase of catalyst. As the reactants and catalyst suspension passes upwardly through the reaction zone the suspension passes through gas bubble dispersing means maintained within the reaction path before the products thereof pass into an enlarged section of the vessel promoting the separation of entrained catalyst from the upflowing vaporous reaction products by a reduction in velocity of the upflowing suspension. A further separation of catalyst from product vapors is accomplished by cyclonic separation means. A water phase comprising water soluble reactants and/or products recovered from the reaction products may be used as quench fluid in combination with catalyst recycle for controlling the exothermic reaction temperature rise. The quench fluid in condit 10 and distributor manifold 12 is passed to one or more distributor grids 8 as a partial and/or additional means for controlling generated exothermic reaction temperatures.

In the upper expanded portion of vessel 2 identified as section 14, the upflowing suspension encounters a reduction in velocity which causes a separation of catalyst from entraining vapors. The vapors pass through cyclonic separation means represented by separators 16 and 20 provided with suitable catalyst diplegs for returning cyclonically separated catalyst to a more dense mass of catalyst 52 collected in the lower portion of the upper enlarged section 14 of the vessel. Vaporous material denuded of catalyst particles by cyclonic separation are removed from the upper portion of the vessel by conduit 22 communicating with the desuper heating section 24 of fractionation zone 26. In the heat removal section 24 the vaporous material is cooled sufficiently to remove from 100° to 400° of heat by a pump around system using the heavy end product of the reaction performed. This heavy end product comprises $C_{10}$ alkyl benzene and higher boiling material. In separation zone 26, a separation is made in an upper portion thereof to recover a heavy gasoline product fraction in conduit 28 from an overhead product. Conduit 28 may contain a large quantity of water depending on the boiling range of the heavy gasoline desired and/or the number of oxygen atoms per molecule of the reactor feed material. A separation of water and heavy gasoline may be effected in the tower using conventional tower design methods, or an external drum may be installed to effect the hydrocarbon-water separation.

The overhead product fraction is withdrawn by conduit 30 and passed to cooler 32 wherein its temperature is reduced sufficient to provide separator drum 34 with a temperature of about 100° F. In separator drum 34, a gas phase is separated and withdrawn by conduit 36. It may be recycled to the reactor inlet as desired for reasons herein discussed. A water phase comprising water soluble oxygenated compounds is withdrawn by conduit 38 and a hydrocarbon phase comprising a light gasoline product of about 300° F. end point or lighter is withdrawn by conduit 40. A portion of this light gasoline product is recycled as reflux to the fractionating tower by conduit 42.

The water phase separated by conduit 38 may be used in the quench system before or after treatment thereof. In a preferred embodiment this water phase is subjected to distillation to recover a methanol rich phase. To accomplish this end, the water phase in conduit 38 may be partially heated in the heat exchanger 44 in the pump around system comprising conduits 44 and 46 in the bottom or lower portion of tower 26. That is, heavy end material not withdrawn from the system is returned to the tower by conduit 48 after passing through heat exchanger 44.

The suspension passed upwardly through the reactor passes through a conical baffle arrangement 50 about which a dense fluid bed of separated catalyst 52 is collected. The catalyst collected in bed 52 may be stripped if desired. A major catalyst stream 54 is withdrawn for recycle to the bottom portion of the reactor vessel 2 and introduced by conduit 4. A portion or portions of this recycle stream may be separated and cooled for introduction in upper portions of the vessel as by conduit 56 and 58 provided with solids cooler 60 and 62 respectively. Introduction of cooled catalyst at spaced apart intervals is used for temperature control within the reactor.

A minor catalyst stream is withdrawn from the bed of catalyst 52 by conduit 64 provided with flow control valve 66 for passage to catalyst regeneration. This may be a continuous or intermittent catalyst withdrawal and this is usually considered only a slip stream of catalyst separated from the major catalyst system above discussed. This catalyst stream may be stripped in a vessel not shown before effecting regeneration thereof.

In the chemical reactions contemplated by this invention, the buildup of carbonaceous deposits on the catalyst generally occurs at a very slow rate requiring an infrequent regeneration of the catalyst. Thus, it is contemplated withdrawing only a slip stream of catalyst as mentioned above from the main reactor system and catalyst recirculation arrangement for regeneration purposes. in a catalyst regeneration zone 68 catalyst may be regenerated in a dense or dispersed phase fluid catalyst regeneration arrangement which is used on a continuous or intermittent basis. On the other hand, the regeneration zone 68 may comprise a sequence of riser regeneration zones to which fresh regeneration gas is passed to the inlet of each riser in such an arrangement for temperature control. It is preferred that the regeneration gas such as air or other suitable oxygen containing regeneration gas be treated to reduce its moisture content not to exceed about 20 ppm.

In the arrangement of FIG. I, regeneration gas is introduced to the lower portion of the regenerator by conduit 70 communicating with a distributor grid 72. Regeneration flue gas is withdrawn from the top of the regenerator by conduit 71 after passage through cyclonic separation equipment not shown for the removal of catalyst fines. The regenerated catalyst is withdrawn by conduit 76 containing valve 78 and returned to the bottom portion of the reaction zone for admixture with recycled catalyst in conduit 54 communicating with a riser mixing conduit 4. Cooling of the regenerated catalyst may be required. Regeneration of the catalyst by burning carbonaceous deposits will normally be accomplished at a relatively low temperature selected from within the range of 750° to about 1400° F. but preferably 750° to 1100° F.; pressures within the range of 0 to 100 psig, but preferably less than 50 psig. A sequence of riser regeneration steps is most desirable since the temperature of the catalyst may be more easily controlled by sequential addition of oxygen containing gas and the level of moisture contacting the catalyst may be controlled with a greater precision.

In the arrangement of FIG. II there is shown a dispersed catalyst phase short contact time riser conversion zone for chemically reacting methanol in the presence of ZSM-5 type crystalline zeolites to produce particularly aromatics. In this arrangement the recycled catalyst is used or injected after cooling thereof at spaced apart intervals to the riser for cooling and controlling the reaction temperature within the dispersed phase riser. Also the methanol reactant, a product recycle rich in methanol or both may also be used alone or in conjunction with the introduced catalyst for controlling the exothermic reaction temperatures encountered. in any of these arrangements it is important to restrict the reaction temperatures not to exceed about 1200° F.

In the specific arrangement of FIG. II, a methanol feed is introduced by conduit 80 to a distributor manifold comprising feed inlets 82, 84 and 86 provided with suitable control valves. A recycled methanol rich stream obtained as discussed above with respect to FIG. I is introduced to the feed inlet manifold by conduit 88 and may be separated from the fresh methanol feed by valve 90. The methanol feed in conduit 82 is combined with recycle catalyst in conduit 92 to form a suspension in the bottom portion of riser 94 at an elevated temperature within the range of 800° to 1200° F. Fresh regenerated catalyst adjusted to a proper temperature may be added to the bottom portion of the riser by conduit 96. The suspension comprising methanol reactant and catalyst is passed upwardly through the riser under reaction conditions controlled as herein described to provide a reactant residence time within the range of 0.5 to 10 seconds. The riser may be provided with one or more cross sectional means not shown for dispersing any formed gas bubbles in the suspension. The upper discharge end of riser 94 is expanded by a conical baffle 98 and capped by a distributor grid 100 in the expanded riser discharge or outlet. The suspension passed through the riser, passes through the conical section and distributor grid placed over the top thereof into an enlarged catalyst separating and settling vessel about the upper end of the riser. The suspension is caused to separate in the enlarged vessel by a velocity reduction into a vaporous product phase and a catalyst phase. The separated catalyst is collected as a dense fluid bed of catalyst 104 about the upper end of the riser. However, in the event that more residence time is desired and required for methanol conversion as herein desired, the upper level of the dense fluid bed of catalyst may be above the riser outlet discharge grid so that the reactants must pass through a dense fluid mass of catalyst. A portion of the dense fluid bed of collected catalyst may be withdrawn by conduit 102 for passage to catalyst regeneration as discussed above. However, the major portion of the collected catalyst is withdrawn from the dense bed of catalyst 104 by conduit 92 for recycle as herein provided.

A portion of the catalyst withdrawn by conduit 92 may be passed by conduit 106 provided with cooler 108 to an upper portion of riser 94 for temperature control of the suspension in the riser. Another portion of the catalyst in conduit 92 may be passed by conduit 110 provided with cooler 112 to a lower intermediate portion of the riser for temperature control of the suspension. Also, as suggested above, recycled methanol rich liquid material recovered from the product of the operation as discussed with respect to FIG. I may be introduced alone or with the recycled catalyst introduced at spaced apart intervals. Also part of the methanol feed many be used in the same manner.

The vaporous products of reaction separated in the upper enlarged vessel 114 by reduced velocity conditions and cyclonic means 116 provided with diplegs 118 pass into a plenum chamber for withdrawal by conduit 120. The vaporous product in conduit 120 is passed to product recovery equipment similar to that described with respect to FIG. I.

When operating within the systems and processing concepts of FIGS. I and II discussed above, it is desirable under some circumstances to maintain a relatively minimum instantaneous concentration of methanol relative to formed aromatic rings in the gas phase in contact with the catalyst. This may be accomplished to some considerable extent by selecting and providing operating conditions comprising very short reactant residence time wherein methanol and methyl ether fed to the catalyst system are reacted to form primarily olefins very rapidly and preferably before aromatic ring formation occurs thereby restricting the formation of highly methylated alkyl aromatics. Thus the system of FIG. II can be operated to form selected olefins for chemical use. On the other hand, a desired restriction may be obtained by providing conditions within the catalyst system so that the methanol reactant is strongly adsorbed on the surface of the catalyst where it dehydrates forming carbon-hydrogen fragments which combine to form olefins preferentially rather than alkylating available aromatics. The above operating functions are particularly promoted by the use of high ratios of catalyst to reactant feed; thus there is provided a large number of active catalyst sites for converting the methanol feed. It is therefore desired that the catalyst to reactant (methanol) ratio be greater than 20 and preferably it should be within the range of 30 to 60. Providing such a high ratio of catalyst to methanol reactant greatly increases the probability that the methanol is adsorbed by the catalyst because it is more polar. Once adsorbed the probability is high that the methanol will dehydrate, form a mobile $C_1$ fragment which can then polymerize to form olefins and cyclize to aromatics rather than form methyl ether and methylate aromatics to avoid forming durene. The more simple alkyl aromatics are preferred as product of the operation.

To assist with accomplishing the above objectives, it is intended that gaseous diluents such as steam or any other suitable relatively inert gaseous material be employed with the methanol feed in sufficient quantity to accomplish the upward flow of catalyst particles in the reactor within the restricted limits of catalyst to methanol feed ratios above recited and desired. As pointed out above during discussion of FIG. I, the gaseous material withdrawn by conduit 36 may be used at least partially for this purpose. This gas stream will comprise hydrocarbons such as $C_2$, $C_3$ and $C_4$ olefins, propane, isobutane, n-butane with lesser amounts of methane and ethane. Small amounts of $H_2$, CO and $CO_2$ may be present. In addition, some quantity of oxygen compounds such as dimethyl ether and methanol may comprise this stream.

Referring now to FIG. III there is shown diagrammatically in side by side relationship a reactor system comprising an upflowing dispersed catalyst phase exothermic conversion of reactant material adjacent to an upflowing dispersed catalyst phase regeneration system. In this combination, provisions are made for recycling regenerated catalyst to the regenerator after cooling thereof and catalyst separated from the upflowing reactant and products of reaction is recycled in part to the inlet to the reaction zone. in the arrangement of FIG. III, the reactant feed material which may be a lower alcohol, an ether product of said lower alcohols or a mixture thereof is introduced either by conduit 122 alone or by conduit 124 alone. The feed introduced by conduit 124 to a manifold 126 supplies the feed to conduits 128, 130 and 132 each communicating with a plurality of heat exchange tubes 134, 136 and 138 respectively placed across the reactor cross section to form a gas dispersing grid. The tube sections 134, 136 and 138 are spaced apart from one another in the vertical heights of the reactor vessel in a manner to form a plurality of gas bubble break-up and dispersing means. Screens or other additional gas bubble dispersing means may be used with and placed adjacent the pipes used as heat exchange pipes for preheating the feed charged to the system by conduit 124. The preheated feed is collected by manifold 140 in communication with feed inlet conduit 122. The feed material introduced and temperature adjusted as discussed above is admixed with recycled catalyst in conduit 142 adjusted to a desired temperature and with temperature adjusted regenerated catalyst in conduit 144 in an amount to provide a suspension at a temperature of about 550° F. Thus catalyst coolers may be provided in conduits 142 and 144. The suspension is then passed upwardly through a restricted riser mixing zone 146 of desired length and then into the lower portion of larger diameter upwardly extending reaction zone. A reactant-catalyst distributor grid means 148 is provided in the lower cross section of the enlarged reaction zone for distributing the upflowing suspension across the reactor cross section. The suspension thus introduced preferably passes upwardly through the reaction zone on a once through basis without reactant recycle within the upflowing suspension under exothermic heat generating conditions during the restructuring of the introduced feed to olefins and/or gasoline boiling components comprising aromatics and isoparaffins. It is preferred to pass the suspension upwardly through the reactor under conditions restricting the temperature preferably not to exceed about 800° F. and the temperature must not exceed about 1000° F. Thus the suspension restricted to the catalyst reactant ratio above identified may be a dispersed catalyst phase system or it may be a more dense suspended phase of catalyst particles of reduced catalyst activity. The suspension in its upward travel is confined by a wall 150, generally cylindrical in shape, which is open at its upper end and discharges into an upper enlarged catalyst separating section of the reactor vessel. In the enlarged separating section of the vessel, the suspension is separated both by hindered settling and by cyclonic separation in a plurality of cyclonic separators 152 and 154 provided with catalyst diplegs for passing separated catalyst to a bed of catalyst in a stripping zone. The catalyst stripping zone may be an annular zone above the cylindrical reaction zone or it may be one or more separate vertical sections for collecting catalyst separated from products of reaction requiring stripping before further use. In any of these stripping arrangements, the separated catalysts pass downwardly countercurrent to rising stripping gas introduced by conduits 156 and 158. A portion of the stripped catalyst at an elevated temperature within the range of 600° to 1000° F. is recycled to riser 146 by conduit 142. Another portion of the stripped catalyst is passed by conduit 160 to a riser regenerator 162 for admixture with oxygen containing regeneration gas introduced by conduit 164. in this arrangement, a suspension of catalyst in regeneration gas is formed and passed upwardly through the riser regenerator under conditions preferably restricting the regeneration temperature not to exceed about 1100° F. On some occasions the regenerator may reach a higher temperature up to about 1500° F. but such a high temperature should not be sustained, is considered undesirable, and should be avoided. In the operating arrangement of FIG. III it is intended to restrict the level of deposited carbon on the catalyst to a relatively low level. To accomplish this, the catalyst circulation rate of the system is controlled to limit incremental carbon laydown on the catalyst ($\Delta$ C) to not exceed one weight percent and preferably it is limited to be less than one weight percent. However, in the even that a higher carbon build-up is experienced in the reactor, it is contemplated recycling regenerated catalyst from the regenerator stripper back the regenerator spent catalyst inlet. This recycled regenerated catalyst may be first cooled in the stripping step and/or it may be cooled indirectly in a separate air cooler, water cooler or with liquid methanol before admixture with catalyst to be regenerated to assure that the regenerator is maintained below a maximum desired temperature. Relying upon any one or a combination of these operating variables permits maintaining the regeneration of the catalyst at a temperature not substantially exceeding about 1100° F. and preferably not above 1000° F.

The suspension in riser 162 is passed upwardly therethrough under carbon burning conditions before discharged into an enlarged settling zone 166 provided with a plurality of cyclonic separation means 168 provided with catalyst diplegs for passing separated catalyst to a separate bed of catalyst in a stripping zone in the lower portion of zone 166. The bed of regenerated catalyst is stripped with a suitable stripping gas such as steam introduced by conduits 168 and 170. Regenerated catalyst is withdrawn by conduit 172. A portion of the regenerated catalyst is passed through a cooler 174 and then by conduit 176 for admixture with coke deactivated catalyst in conduit 160 being passed to riser 162. A portion of the regenerated catalyst is passed by conduits 172 and 144 to riser 146 as discussed above. Regeneration flue gases are withdrawn by conduit 178. Products of reaction are withdrawn by conduit 180 and passed to suitable recovery equipment not shown. It may be similar to that shown in FIG. I.

It is to be understood that in the arrangement of FIG. III that either vapor or liquid methanol (or lower alcohols) may be employed as feed to the process and the conversion of the lower alcohols or ether derivatives thereof to gasoline boiling constituents is particularly enhanced by the use of reactant plug flow, that is, no substantial reactant back mixing operating conditions at temperatures less than 1000° F. and restricted preferably to within the range of about 500° to 900° F.

Having thus generally described the method and means of the present invention and discussed specific embodiments related thereto, it is to be understood that no undue restrictions are to be imposed by reason thereof except as defined by the following claims.

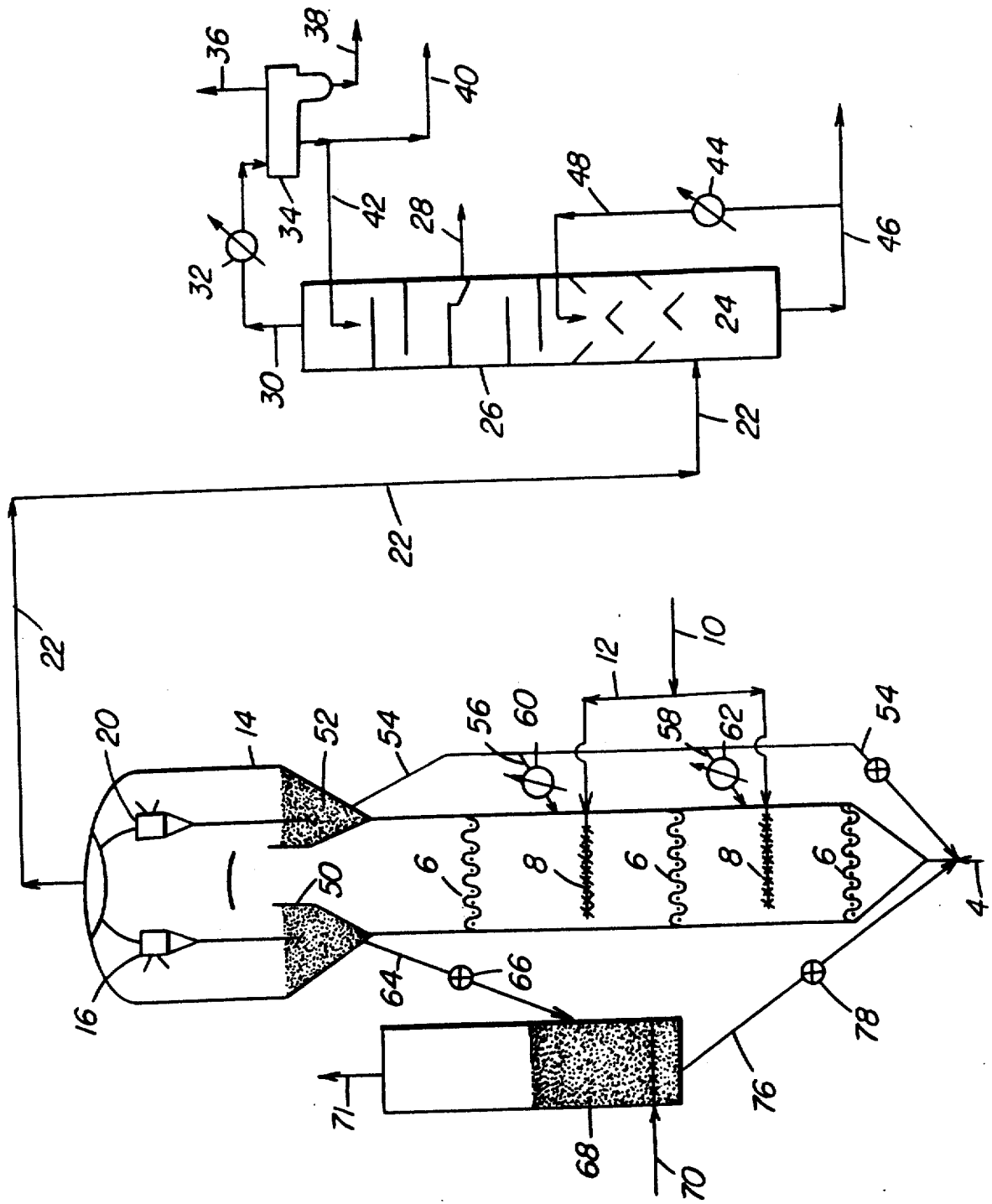

What is claimed is:

1. In a fluid catalyst operation for effecting the exothermic conversion of chemical reactants comprising hetero compounds selected from the group consisting of alcohols, halides, mercaptans, sulfides, amines, ethers and carbonyl compounds over catalyst particles comprising a crystalline zeolite selected from a class of crystalline zeolites represented by ZSM-5 crystalline zeolite providing a pore opening greater than 5 Angstroms, a silica-to-alumina ratio greater than 12 and a constraint index in the range of 1 to 12, wherein said catalyst with carbonaceous deposit is passed to a catalyst regeneration zone, wherein a mixture of catalyst particles and a reactant hetero compound in a ratio greater than 20 to 1 is formed at a temperature in the range of 400° to 900° F and is passed upwardly through a confined reaction zone as a suspension through a plurality of gas bubble dispersion zones within the reaction zone, and the suspension in the reaction zone is restricted to an exothermic temperature rise not to exceed 100°, followed by separating the suspension upon discharge from the reaction zone into a gasiform product phase and a catalyst particle phase, and directly recycling a portion of the separated catalyst particle phase for admixture with reactant material charged to said reaction zone; the improvement which comprises preheating said chemical reactants by indirect heat exchange within said gas bubble dispersion zones before being introduced into said reaction zone and maintaining the catalyst circulation rate to limit incremental carbon laydown to no more than 1 weight percent.

2. The process of claim 1, wherein said hetero compound is methanol.

3. The process of claim 1, wherein the incremental carbon increase is controlled by passing regenerated catalyst containing excessive carbon to the inlet of said regeneration zone.

4. The process of claim 3 wherein a portion of the regenerated catalyst is cooled, mixed with carbon containing catalyst to be regenerated and then contacted with regeneration gas in a riser regeneration operation.

* * * * *

UNITED STATES PATENT AND TRADEMARK OFFICE
CERTIFICATE OF CORRECTION

PATENT NO. : 4,071,573
DATED : January 31, 1978
INVENTOR(S) : HARTLEY OWEN and PAUL B. VENUTO It is certified that error appears in the above-identified patent and that said Letters Patent are hereby corrected as shown below:

Column 2, line 65            "helimum" should be --helium--.

Column 4, line 17            "sluminum" should be --aluminum--.

Column 7, line 17            "condit" should be --conduit--.

Column 8, line 33            "in" should be --In--.

Column 9, line 10            "in" should be --In--.

Column 11, lines 66 & 67     After 164. "in" should be --In--.

Column 12, line 13           "even" should be --event--.

Figure 1 and the drawing Figure which appears on the cover sheet should appear as per attachment.

Signed and Sealed this

Sixth Day of June 1978

[SEAL]

Attest:

RUTH C. MASON
Attesting Officer

DONALD W. BANNER
Commissioner of Patents and Trademarks